US012584166B2

(12) United States Patent
Liu et al.

(10) Patent No.: US 12,584,166 B2
(45) Date of Patent: Mar. 24, 2026

(54) METHOD AND SYSTEM FOR DETECTING MTDNA MUTATIONS

(71) Applicant: GUANGZHOU INSTITUTES OF BIOMEDICINE AND HEALTH, CHINESE ACADEMY OF SCIENCES, Guangzhou (CN)

(72) Inventors: Xingguo Liu, Guangzhou (CN); Liang Yang, Guangzhou (CN); Xiaobing Lin, Guangzhou (CN); Haite Tang, Guangzhou (CN)

(73) Assignee: GUANGZHOU INSTITUTES OF BIOMEDICINE AND HEALTH, CHINESE ACADEMY OF SCIENCES, Guangzhou (CN)

( * ) Notice: Subject to any disclaimer, the term of this patent is extended or adjusted under 35 U.S.C. 154(b) by 1150 days.

(21) Appl. No.: 17/538,594

(22) Filed: Nov. 30, 2021

(65) Prior Publication Data

US 2022/0090188 A1     Mar. 24, 2022

Related U.S. Application Data

(63) Continuation of application No. PCT/CN2020/077422, filed on Mar. 2, 2020.

(30) Foreign Application Priority Data

Jun. 13, 2019     (CN) .......................... 201910509687.4

(51) Int. Cl.
*C12Q 1/6858*          (2018.01)
*C12N 15/10*          (2006.01)
          (Continued)

(52) U.S. Cl.
CPC ....... *C12Q 1/6858* (2013.01); *C12N 15/1093* (2013.01); *C12Q 1/6827* (2013.01);
          (Continued)

(58) Field of Classification Search
None
See application file for complete search history.

(56) References Cited

U.S. PATENT DOCUMENTS

2017/0101673 A1*   4/2017   Nygren .................. C12Q 1/686

FOREIGN PATENT DOCUMENTS

CN          106755456          5/2017
WO      WO-2009032781 A2 *   3/2009   ............. C12Q 1/686

OTHER PUBLICATIONS

Qamar et al. (Optimization of conditions to extract high quality DNA for PCR analysis from whole blood using SDS-proteinase K method, Saudi J. Biol. Sci., published Sep. 10, 2016. (Year: 2016).*
(Continued)

*Primary Examiner* — Heather Calamita
*Assistant Examiner* — Elizabeth Rose Lafave
(74) *Attorney, Agent, or Firm* — Hodgson Russ LLP

(57)          ABSTRACT

Provided are a method and a system for detecting mtDNA mutations. Specifically, provided is a method for detecting mtDNA mutations in trace cells, comprising: (a) extracting mtDNA in trace cells, the number of trace cells being 1 to 4; (b) performing PCR amplification on different predetermined regions of the mtDNA to acquire amplification products of the different predetermined regions, the different predetermined regions of the mtDNA being superimposed to form the full-length mtDNA; (c) mixing the amplification products of the different predetermined regions to obtain an mtDNA full-length nucleic acid sequencing library; (d) sequencing the nucleic acid sequencing library to obtain sequencing results; and (e) on the basis of the sequencing results, determining mtDNA mutations in the trace cells to be tested.

7 Claims, 3 Drawing Sheets

Specification includes a Sequence Listing.

(51) Int. Cl.
    *C12Q 1/6827*     (2018.01)
    *C12Q 1/686*     (2018.01)
    *C12Q 1/6869*     (2018.01)
    *C12Q 1/6876*     (2018.01)
    *C12Q 1/6883*     (2018.01)
    *C40B 50/06*     (2006.01)

(52) U.S. Cl.
    CPC ........... *C12Q 1/686* (2013.01); *C12Q 1/6869* (2013.01); *C12Q 1/6876* (2013.01); *C12Q 1/6883* (2013.01); *C40B 50/06* (2013.01); *C12Q 2531/113* (2013.01); *C12Q 2600/156* (2013.01)

(56)          References Cited

OTHER PUBLICATIONS

Of Rooney et al. (PCR Based Determination of Mitochondrial DNA Copy Number in Multiple Species, Methods Mol. Biol., published Feb. 1, 2015) (Year: 2015).*

Tuppen et al. (Mitochondrial DNA mutations and human diseases, Biochimica et Biophysica Acta (BBA) Bioenergetics, published Feb. 2010). (Year: 2010).*

Morris et al., "Subcellular Genomics: Pervasive within-mitochondrion SNV heteroplasmy revealed by single mitochondrion sequencing," Cell Rep., Dec. 5, 2017, vol. 21, No. 10, pp. 2706-2713.

WIPO, International Search Report for International Application No. PCT/CN2020/077422, May 21, 2020.

* cited by examiner

METHOD AND SYSTEM FOR DETECTING MTDNA MUTATIONS

CROSS-REFERENCE TO RELATED APPLICATIONS

This application is a continuation application of International Application No. PCT/CN2020/077422 filed on Mar. 2, 2020, which claims a priority to, and the benefits of, Chinese Patent Application No. 201910509687.4 filed on Jun. 13, 2019, the entire contents of which are incorporated herein by reference.

SEQUENCE LISTING

The instant application contains a Sequence Listing which has been submitted electronically in txt format and is hereby incorporated by reference in its entirety. Said txt copy was created on Jun. 13, 2019, is named "PIDC3191816PUS-Sequence_Listing" and is 2842 bytes in size.

FIELD

The present disclosure relates to the field of bioengineering, in particular to a method and system for detecting mtDNA mutations.

BACKGROUND

Age is one of the key factors affecting male and female fertility. The female usually has highest fertility rate at the age of 24 years old and decreased fertility rate after the age of 30 years old, and rarely get pregnant after the age of 50 years old. In recent years, the phenomenon of infertility and low fertility has increasingly increased. More and more people believe that mitochondria play an important role in infertility caused by age and environment. However, currently technology for analyzing mtDNA mutations in a single egg does not exist.

Therefore, it is of great significance to establish a method capable of analyzing the mtDNA mutations in a single egg cell.

SUMMARY

The present disclosure is based on inventors' discovery and understanding of the following facts and problems.

The difficulty on PCR amplification of mtDNA sequences in a single egg lies in that many sequences of mitochondrial nuclear pseudogenes which are similar to the mtDNA sequences exist in the nucleus. Further, a very small number of egg cells can be obtained from a patient, generally merely several egg cells, and thus genome cannot be extracted from the small number of egg cells. Thus, it is very difficult to obtain enough egg cells to analyze mtDNA mutations, especially considering the presence of mitochondrial nuclear pseudogenes. After a lot of experimental exploration, the present inventors have found that the detection method of the present disclosure can accurately detect mtDNA mutations in a trace amount of cells and can even accurately analyze mtDNA mutations as low as a single cell, thus achieving a breakthrough in the detection of mtDNA mutations in a single egg cell.

Thus, in a first aspect of the present disclosure, the present disclosure in embodiments proposes a method for detecting mitochondrial DNA (mtDNA) mutations in cells. The method can be used for non-diagnostic purposes, such as scientific research, for example, for studying the causes of mtDNA mutations.

According to embodiments of the present disclosure, the method comprises:

(a) extracting mtDNA in the cells;

(b) subjecting different predetermined regions of the mtDNA to PCR amplification to obtain amplification products of the different predetermined regions, wherein the different predetermined regions of the mtDNA are superimposed to form a full-length mtDNA;

(c) mixing the amplification products of the different predetermined regions to obtain a nucleic acid sequencing library of the full-length mtDNA;

(d) subjecting the nucleic acid sequencing library to sequencing to obtain a sequencing result; and (e) determining the mtDNA mutations in the cells based on the sequencing result.

According to embodiments of the present disclosure, the cells are a trace amount of cells. According to embodiments of the present disclosure, the number of the trace amount of cells is one to four.

According to embodiments of the present disclosure, the cell can be an egg cell. According to embodiments of the present disclosure, the cell can be a non-egg cell, such as a somatic cell. The present inventors have found that the method according to the embodiments of the present disclosure can effectively analyze mtDNA mutations in a trace amount of cells (such as a single cell), with high accuracy and high sensitivity.

According to embodiments of the present disclosure, the method as described above may further include at least one of the following additional technical features.

According to embodiments of the present disclosure, the cell is an egg cell. The method in existing technology cannot analyze mtDNA mutations in an egg cell. The present inventors have found that the method according to the embodiments of the present disclosure can effectively analyze mtDNA mutations in egg cells, even in a single egg cell, with high accuracy and high sensitivity.

According to embodiments of the present disclosure, the different predetermined regions of the mtDNA comprises a mitochondrial genome 3561-9794 region, a mitochondrial genome 9795-14567 region, a mitochondrial genome 14562-139 region and a mitochondrial genome 115-3560 region. The present inventors have found that when different predetermined regions of the mtDNA are divided according to the manner as described above, the full length of the mitochondrial genome can be effectively covered. Therefore, the detection method according to the embodiments of the present disclosure exhibits higher accuracy and higher sensitivity.

According to embodiments of the present disclosure, primers for the PCR amplification are of nucleotide sequences shown in SEQ ID NOs: 1-8. The present inventors have found that when the primers are of the nucleotide sequences shown in SEQ ID NOs: 1 to 8, it is capable of effectively amplifying the four regions covering the full-length mtDNA of a single egg cell. Therefore, the detection method according to the embodiments of the present disclosure exhibits higher accuracy and higher sensitivity. Among them, when the primers are of the nucleotide sequences shown in SEQ ID NOs: 1-2, a target region for the PCR amplification is the mitochondrial genome 3561-9794 region. When the primers are of the nucleotide sequences shown in SEQ ID NOs: 3-4, a target region for the PCR amplification is the mitochondrial genome 9795-14567 region. When the primers are of the nucleotide sequences shown in SEQ ID NOs: 5-6, a target region for the PCR amplification is the mitochondrial genome 14562-139 region. When the primers are of the nucleotide sequences shown in SEQ ID NOs: 7-8, a target region for the PCR amplification is the mitochondrial genome 115-3560 region.

According to embodiments of the present disclosure, in step (a), extracting mtDNA in the cells is performed by subjecting the cells to a lysis treatment. In some embodiments, the lysis treatment is performed in a lysis solution.

According to embodiments of the present disclosure, the lysis solution in a volume of 20 μL comprises 17 to 18 μL of $H_2O$ such as 17.2 μL, 17.4 μL, 17.5 μL, 17.75 μL or 17.9 μL of $H_2O$, 1 to 3 μL of 10×KOD buffer such as 1.5 μL, 2.0 μL or 2.5 μL of 10×KOD buffer, and 0.2 to 0.3 μL of proteinase K such as 0.22 μL, 0.24 μL, 0.25 μL, 0.26 μL or 0.28 μL of proteinase K. Thus, the lysis solution exhibits a better lysis effect and the mtDNA obtained by extraction has higher amount and higher purity. Therefore, the method for detecting mtDNA mutations in a trace amount of cells according to the embodiments of the present disclosure exhibits higher accuracy and higher sensitivity.

According to embodiments of the present disclosure, a ratio of the cells (in number) to the lysis solution (in volume) is 1 to 4 cells per 20 μL lysis solution. The present inventors have found that when a ratio of the cells to the lysis solution is 1 to 4 cells per 20 μL lysis solution, such as one cell per 20 μL lysis solution, two cells per 20 μL lysis solution, three cells per 20 μL lysis solution or four cells per 20 μL lysis solution, the lysis treatment has a better lysis effect and the mtDNA obtained by extraction has higher amount and higher purity. Therefore, the method for detecting mtDNA mutations in a trace amount of cells according to the embodiments of the present disclosure exhibits higher accuracy and higher sensitivity.

According to embodiments of the present disclosure, the lysis treatment comprises lysing at 50-60° C. such as 51° C., 53° C., 55° C., 57° C., 59° C. or 60° C. for 40-50 minutes such as 41 minutes, 43 minutes, 45 minutes, 47 minutes or 49 minutes; subsequently at 90-100° C. such as 92° C., 94° C., 96° C., 98° C. or 100° C. for 1-10 minutes such as 1 minute, 3 minutes, 5 minutes, 7 minutes or 9 minutes; and holding at 1-10° C. such as 2° C., 4° C., 6° C., 8° C. or 10° C. The present inventors have found that when the lysis treatment is performed according to the lysis procedure as described above, the lysis treatment has a better lysis effect and the mtDNA obtained by extraction has higher amount and higher purity. Therefore, the method for detecting mtDNA mutations in a trace amount of cells according to the embodiments of the present disclosure exhibits higher accuracy and higher sensitivity.

According to embodiments of the present disclosure, when the mitochondrial genome 3561-9794 region is subjected to PCR amplification, the PCR amplification is performed by a reaction procedure of:

| 95° C. | 5 minutes | |
| 94° C. | 30 seconds | 40 cycles |
| 57° C. | 45 seconds | |
| 68° C. | 6 minutes and 30 seconds | |
| 68° C. | 10 minutes | |
| 4° C. | holding | |

When the mitochondrial genome 9795-14567 region is subjected to PCR amplification, the PCR amplification is performed by a reaction procedure of:

| 95° C. | 5 minutes | |
| 94° C. | 30 seconds | 40 cycles |
| 57° C. | 45 seconds | |
| 68° C. | 5 minutes | |
| 68° C. | 10 minutes | |
| 4° C. | holding | |

When the mitochondrial genome 14562-139 region is subjected to PCR amplification, the PCR amplification is performed by a reaction procedure of:

| 95° C. | 5 minutes | |
| 94° C. | 30 seconds | 40 cycles |
| 57° C. | 45 seconds | |
| 68° C. | 2 minutes | |
| 68° C. | 10 minutes | |
| 4° C. | holding | |

When the mitochondrial genome 115-3560 region is subjected to PCR amplification, the PCR amplification is performed by a reaction procedure of:

| 95° C. | 5 minutes | |
| 94° C. | 30 seconds | 40 cycles |
| 57° C. | 45 seconds | |
| 68° C. | 3 minutes and 30 seconds | |
| 68° C. | 10 minutes | |
| 4° C. | holding | |

In a second aspect of the present disclosure, the present disclosure in embodiments proposes a system for detecting mtDNA mutations in cells. According to embodiments of the present disclosure, referring to FIG. 4, the system comprises:

a nucleic acid extraction device 100, configured to extract mtDNA in the cells;

a PCR amplification device 200, connected to the nucleic acid extraction device 100 and configured to subject different predetermined regions of the mtDNA to PCR amplification to obtain amplification products of the different predetermined regions, wherein the different predetermined regions of the mtDNA are superimposed to form a full-length mtDNA;

a library construction device 300, connected to the PCR amplification device 200 and configured to mix the amplification products of the different predetermined regions to obtain a nucleic acid sequencing library of the full-length mtDNA;

a sequencing device 400, connected to the library construction device 300 and configured to subject the nucleic acid sequencing library to sequencing to obtain a sequencing result; and a mutation determination device 500, connected to the sequencing device 400 and configured to determine the mtDNA mutations in the cells based on the sequencing result.

According to embodiments of the present disclosure, the cells are a trace amount of cells. According to embodiments of the present disclosure, the number of the trace amount of cells is one to four.

According to embodiments of the present disclosure, the cell can be an egg cell. According to embodiments of the present disclosure, the cell can be a non-egg cell, such as a somatic cell. The present inventors have found that the system according to the embodiments of the present disclosure can effectively analyze mtDNA mutations in a trace amount of cells (such as a single cell), with high accuracy and high sensitivity.

According to embodiments of the present disclosure, the system as described above may further include at least one of the following additional technical features.

According to embodiments of the present disclosure, the cell is an egg cell. The method in existing technology cannot analyze mtDNA mutations in an egg cell. The present inventors have found that the system according to the embodiments of the present disclosure can be useful in analyze mtDNA mutations in egg cells, even in a single egg cell, with high accuracy and high sensitivity.

According to embodiments of the present disclosure, the different predetermined regions of the mtDNA comprises a mitochondrial genome 3561-9794 region, a mitochondrial genome 9795-14567 region, a mitochondrial genome 14562-139 region and a mitochondrial genome 115-3560 region. The present inventors have found that when different predetermined regions of the mtDNA are divided according to the manner as described above, the full length of the mitochondrial genome can be effectively covered. Therefore, the detection system according to the embodiments of the present disclosure exhibits higher accuracy and higher sensitivity.

According to embodiments of the present disclosure, primers for the PCR amplification are of nucleotide sequences shown in SEQ ID NOs: 1-8. The present inventors have found that when the primers are of the nucleotide sequences shown in SEQ ID NOs: 1 to 8, it is capable of effectively amplifying the four regions covering the full-length mtDNA of a single egg cell. Therefore, the detection system according to the embodiments of the present disclosure exhibits higher accuracy and higher sensitivity.

According to embodiments of the present disclosure, the nucleic acid extraction device is configured to subject the cells to a lysis treatment to extract mtDNA in the cells. According to embodiments of the present disclosure, the lysis treatment is performed in a lysis solution.

According to embodiments of the present disclosure, the lysis solution in a volume of 20 µL comprises 17 to 18 µL of $H_2O$ such as 17.2 µL, 17.4 µL, 17.5 µL, 17.75 µL or 17.9 µL of $H_2O$, 1 to 3 µL of 10×KOD buffer such as 1.5 µL, 2.0 µL or 2.5 µL of 10×KOD buffer, and 0.2 to 0.3 µL of proteinase K such as 0.22 µL, 0.24 µL, 0.25 µL, 0.26 µL or 0.28 µL of proteinase K. Thus, the lysis solution exhibits a better lysis effect and the mtDNA obtained by extraction has higher amount and higher purity. Therefore, the system for detecting mtDNA mutations in a trace amount of cells according to the embodiments of the present disclosure exhibits higher accuracy and higher sensitivity.

According to embodiments of the present disclosure, a ratio of the cells (in number) to the lysis solution (in volume) is 1 to 4 cells per 20 µL lysis solution. The present inventors have found that when a ratio of the cells to the lysis solution is 1 to 4 cells per 20 µL lysis solution, such as one cell per 20 µL lysis solution, two cells per 20 µL lysis solution, three cells per 20 µL lysis solution or four cells per 20 µL lysis solution, the lysis treatment has a better lysis effect and the mtDNA obtained by extraction has higher amount and higher purity. Therefore, the system for detecting mtDNA mutations in a trace amount of cells according to the embodiments of the present disclosure exhibits higher accuracy and higher sensitivity.

According to embodiments of the present disclosure, the lysis treatment comprises lysing at 50-60° C. such as 51° C., 53° C., 55° C., 57° C., 59° C. or 60° C. for 40-50 minutes such as 41 minutes, 43 minutes, 45 minutes, 47 minutes or 49 minutes; subsequently at 90-100° C. such as 92° C., 94° C., 96° C., 98° C. or 100° C. for 1-10 minutes such as 1 minute, 3 minutes, 5 minutes, 7 minutes or 9 minutes; and holding at 1-10° C. such as 2° C., 4° C., 6° C., 8° C. or 10° C. The present inventors have found that when the lysis treatment is performed according to the lysis procedure as described above, the lysis treatment has a better lysis effect and the mtDNA obtained by extraction has higher amount and higher purity. Therefore, the system for detecting mtDNA mutations in a trace amount of cells according to the embodiments of the present disclosure exhibits higher accuracy and higher sensitivity.

According to embodiments of the present disclosure, when the mitochondrial genome 3561-9794 region is subjected to PCR amplification, the PCR amplification is performed by a reaction procedure of:

| 95° C. | 5 minutes | |
| 94° C. | 30 seconds | 40 cycles |
| 57° C. | 45 seconds | |
| 68° C. | 6 minutes and 30 seconds | |
| 68° C. | 10 minutes | |
| 4° C. | holding | |

When the mitochondrial genome 9795-14567 region is subjected to PCR amplification, the PCR amplification is performed by a reaction procedure of:

| 95° C. | 5 minutes | |
| 94° C. | 30 seconds | 40 cycles |
| 57° C. | 45 seconds | |
| 68° C. | 5 minutes | |
| 68° C. | 10 minutes | |
| 4° C. | holding | |

When the mitochondrial genome 14562-139 region is subjected to PCR amplification, the PCR amplification is performed by a reaction procedure of:

| 95° C. | 5 minutes | |
| 94° C. | 30 seconds | 40 cycles |
| 57° C. | 45 seconds | |
| 68° C. | 2 minutes | |
| 68° C. | 10 minutes | |
| 4° C. | holding | |

When the mitochondrial genome 115-3560 region is subjected to PCR amplification, the PCR amplification is performed by a reaction procedure of:

| 95° C. | 5 minutes | |
| 94° C. | 30 seconds | 40 cycles |
| 57° C. | 45 seconds | |
| 68° C. | 3 minutes and 30 seconds | |
| 68° C. | 10 minutes | |
| 4° C. | holding | |

REFERENCE SIGNS

100: Nucleic acid extraction device

200: PCR amplification device

300: Library construction device

400: Sequencing device

500: Mutation determination device

DETAILED DESCRIPTION OF EMBODIMENTS

Figure 1:
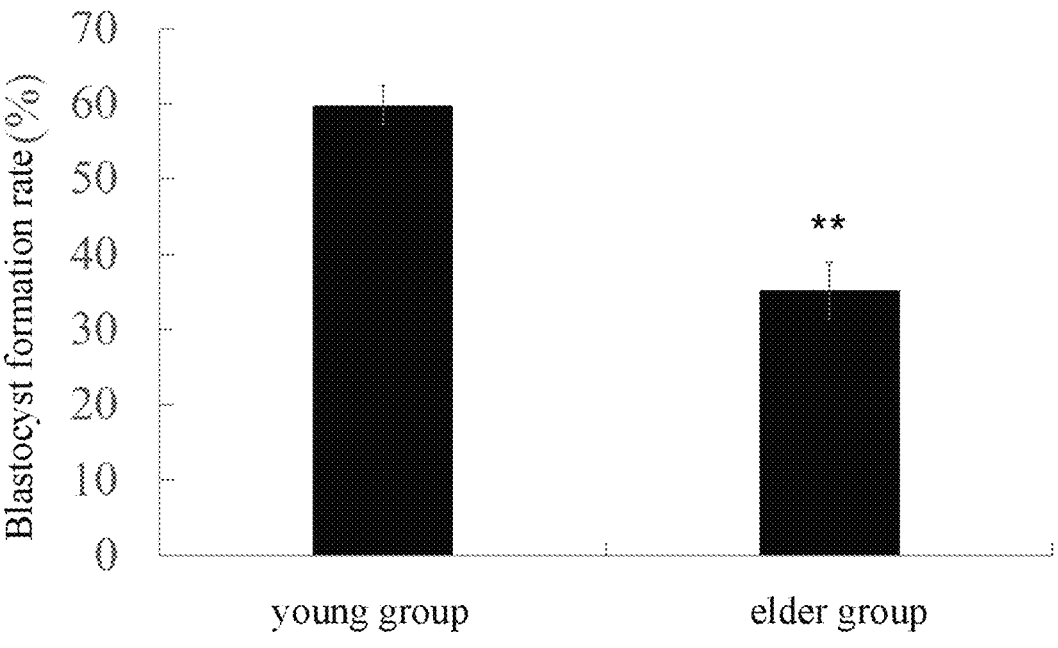
FIG. 1 is a graph showing the blastocyst formation rate of egg cells of elder women and young women according to embodiments of the present disclosure.

The embodiments of the present disclosure are described in detail below and are exemplary. They are intended to explain the present disclosure, but should not be construed as limiting the present disclosure.

The present disclosure relates to PCR amplification and sequencing of the full-length mitochondrial genome of a single egg cell, in particular to a method for detecting mtDNA mutations (such as mutation rate) in a single egg cell of a female patient.

Example 1

The present inventors first designed two sets of primers (a first set of primers and a second set of primers) for amplifying two regions of the full-length mtDNA. It was discovered that although the two sets of primers can be used to amplify mtDNA in non-egg cells such as human mesenchymal stem cell (MSC), human embryonic kidney 293T cells, SK-Hep1 cells, Hela cells or the like, they cannot amplify the two regions of the full-length mtDNA in a single egg cell. Among them, the first and second sets of invalid primers and their sequences are shown in Table 1 and Table 2 as below.

TABLE 1

| First set of invalid primers | |
| --- | --- |
| Primers | Primer sequence |
| 3561-FP | ATGAACCCCCCTCCCCATACCC (SEQ ID NO: 1) |
| 11509-RP | GAGAATGAGTGTGAGGCGTA (SEQ ID NO: 9) |
| 11493-FP | GCCTCACACTCATTCTCAACC (SEQ ID NO: 10) |
| 3560-RP | AGTAGAAGAGCGATGGTGAG (SEQ ID NO: 8) |

TABLE 2

| Second set of invalid primers | |
| --- | --- |
| Primers | Primer sequence |
| h1-9794-R1 | TGTTGAGCCGTAGATGCCGTCGGAAAT (SEQ ID NO: 2) |
| h1-9795-F2 | TTTTTTGTAGCCACAGGCTTCCACGGACT (SEQ ID NO: 3) |
| h1-139-R3 | GAATCAAAGACAGATACTGCGACAT (SEQ ID NO: 6) |
| h1-115-F4 | ATGTCGCAGTATCTGTCTTTGATTC (SEQ ID NO: 7) |

The present inventors further designed three sets of primers (a third set of primers, a fourth set of primers and a fifth set of primers) for amplifying four regions of the full-length mtDNA. It was discovered that when used to amplify mtDNA in non-egg cells such as human MSC cells, 293T cells, SK-Hep1 cells, Hela cells or the like, the three sets of primers all could effectively amplify the four regions covering the full-length mtDNA. Further, the three sets of primers were used for amplification of mtDNA in egg cells. It was found that two sets of primers (the third set of primers and the fourth set of primers) cannot effectively amplify the four regions covering the full-length mtDNA of the egg cell, whereas one set of primers (the fifth set of primers) can effectively amplify the four regions covering the full-length mtDNA of the egg cell. Therefore, the present inventors finally chose the fifth set of primers for subsequent experiments related to detection of mitochondrial mutations in egg cells. Among them, the third, fourth and fifth sets of primers and their sequences are shown in Tables 3 to 5 as below.

TABLE 3

| Third set of invalid primers | |
| --- | --- |
| Primers | Primer sequence |
| 3561-FP | ATGAACCCCCCTCCCCATACCC (SEQ ID NO: 1) |
| 7781-RP | TTCAGACGGTTTCTATTTCC (SEQ ID NO: 11) |
| 7767-FP | TAGAAACCGTCTGAACTATCCT (SEQ ID NO: 12) |
| 11509-RP | GAGAATGAGTGTGAGGCGTA (SEQ ID NO: 9) |
| 11493-FP | GCCTCACACTCATTCTCAACC (SEQ ID NO: 10) |
| 15557-RP | CGGGCTTGATGTGGGGAGGG (SEQ ID NO: 13) |
| 15534-FP | ACACCCCTCCCCACATCAAG (SEQ ID NO: 14) |
| 3560-RP | AGTAGAAGAGCGATGGTGAG (SEQ ID NO: 8) |

TABLE 4

Fourth set of invalid primers

| Primers | Primer sequence |
|---------|-----------------|
| 3561-FP | ATGAACCCCCCTCCCCATACCC (SEQ ID NO: 1) |
| 7781-RP | TTCAGACGGTTTCTATTTCC (SEQ ID NO: 11) |
| 7767-FP | TAGAAACCGTCTGAACTATCCT (SEQ ID NO: 12) |
| 11509-RP | GAGAATGAGTGTGAGGCGTA (SEQ ID NO: 9) |
| 11493-FP | GCCTCACACTCATTCTCAACC (SEQ ID NO: 10) |
| h1-14567-R2 | TGTGGTCGGGTGTGTTATTATTCT (SEQ ID NO: 4) |
| h1-14562-F3 | CCACACCGCTAACAATCAAT (SEQ ID NO: 5) |
| 3560-RP | AGTAGAAGAGCGATGGTGAG (SEQ ID NO: 8) |

TABLE 5

Fifth set of valid primers

| Primers | Primer sequence |
|---------|-----------------|
| 3561-FP | ATGAACCCCCCTCCCCATACCC (SEQ ID NO: 1) |
| h1-9794-R1 | TGTTGAGCCGTAGATGCCGTCGGAAAT (SEQ ID NO: 2) |
| h1-9795-F2 | TTTTTTGTAGCCACAGGCTTCCACGGACT (SEQ ID NO: 3) |
| h1-14567-R2 | TGTGGTCGGGTGTGTTATTATTCT (SEQ ID NO: 4) |
| h1-14562-F3 | CCACACCGCTAACAATCAAT (SEQ ID NO: 5) |
| h1-139-R3 | GAATCAAAGACAGATACTGCGACAT (SEQ ID NO: 6) |
| h1-115-F4 | ATGTCGCAGTATCTGTCTTTGATTC (SEQ ID NO: 7) |
| 3560-RP | AGTAGAAGAGCGATGGTGAG (SEQ ID NO: 8) |

Example 2

Experimental Method

The present inventors further analyzed the clinical data of female patients who underwent intracytoplasmic sperm injection (ICSI) from the cooperative unit. The female patients were divided into young group (not more than 30 years old) and elder group (not less than 38 years old) according to their age. The blastocyst formation rate of the egg cells of 157 female patients who underwent ICSI of the young group and 103 female patients who underwent ICSI of the elder group from May 2017 to March 2018 was subjected to systematical analysis. The experimental results are shown in FIG. 1.

FIG. 1 shows the blastocyst formation rate of the egg cells of the 157 female patients underwent ICSI (the young group) and 103 female patients underwent ICSI (the elder group) in the present disclosure. The results showed that the blastocyst formation rate of the young group was higher than that of the elder group, indicating that the egg cell quality of the elderly female patients was worse than that of the young female patients.

Example 3

Experimental Method

The present inventors collected immature waste eggs from female patients who underwent ICSI from the cooperative unit, in which egg cells from 9 young female patients and 10 elderly female patients were obtained. One to four of immature waste eggs from each patient were placed into a centrifuge tube containing 20 μL of cell lysis buffer. The lysis solution in a volume of 20 μL includes 17.75 μL of H$_2$O, 2.0 μL of 10×KOD buffer and 0.25 μL of proteinase K. The reaction procedure for lysis treatment includes lysing at 55° C. for 45 minutes, subsequently at 94° C. for 5 minutes and holding at 4° C. 5.0 μL of egg cell lysate after the lysis treatment for each patient was taken for PCR amplification of mitochondrial genome. Four pairs of primers were used to amplify mitochondrial genome 3561-9794 region, mitochondrial genome 9795-14567 region, mitochondrial genome 14562-139 region and mitochondrial genome 115-3560 region respectively. These four regions cover the full length of the mitochondrial genome. The primers used are shown in Table 5 as above. Procedure for PCR amplification: denaturation at 95° C. for 5 minutes; 40 cycles including denaturation at 94° C. for 30 seconds, annealing at 57° C. for 45 seconds and extension at 68° C., where the extension time for each region is calculated at 1000 bp per minute, thus the extension time is 6 minutes and 30 seconds for the 3561-9794 region, 5 minutes for the 9795-14567 region, 2 minutes for the 14562-139 region and 3 minutes and 30 seconds for the 115-3560 region; extension at 68° C. for 10 minutes; and holding at 4° C. The amplification products of the four regions were subjected to 1% agarose gel electrophoresis, after which the gel was cut and recovered. The recovered four regions were combined and subjected to next-generation high-throughput sequencing to analyze the mutation rate of the mitochondrial genome. The experimental results are shown in FIG. 2.

Figure 2:
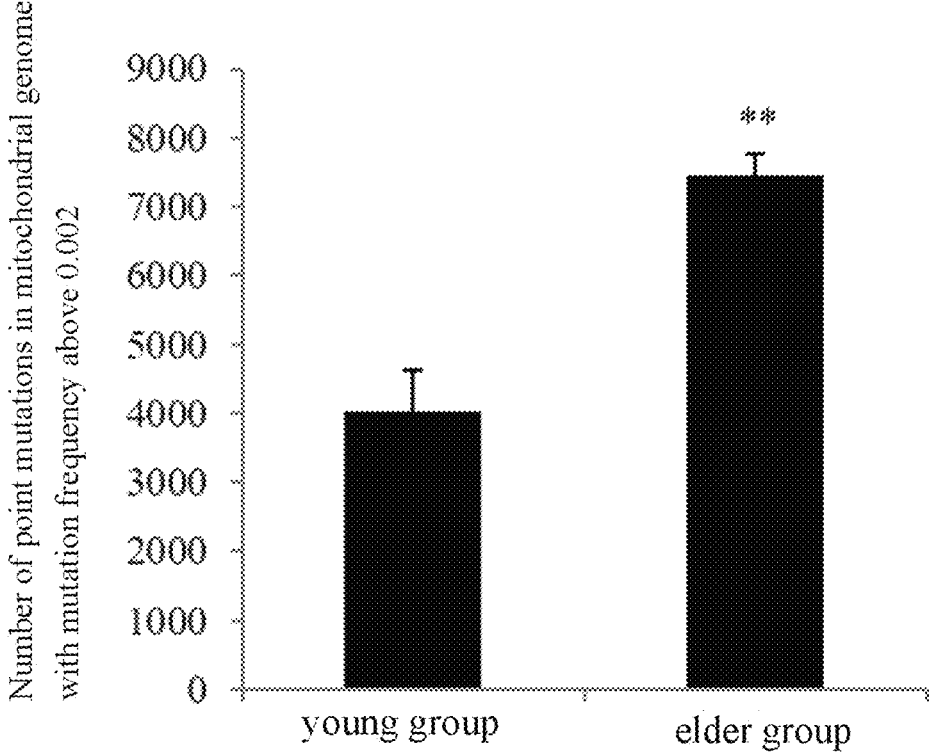
FIG. 2 is a graph showing the number of point mutations in the mitochondrial genome of egg cells of elder women and young women according to embodiments of the present disclosure.

FIG. 2 shows the number of point mutations in mitochondrial genome of egg cells of 9 young female patients and 10 elderly female patients. The results showed that the number of point mutations in mitochondrial genome of the elderly female patients was significantly higher than the number of point mutations in mitochondrial genome of the young female patients.

Example 4

Experimental Method

The present inventors further analyzed the frequency of point mutations in the mitochondrial genome of egg cells based on the results of FIG. 2. The experimental results are shown in FIG. 3.

Figure 3:
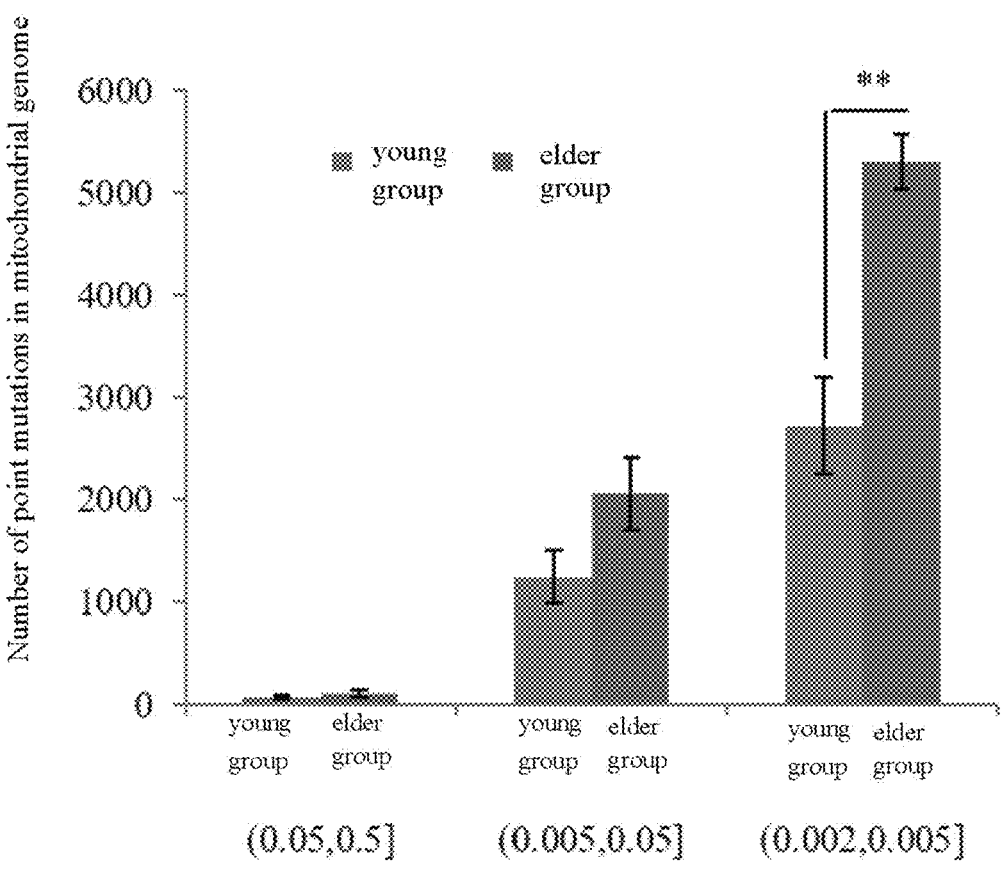
FIG. 3 is a graph showing the frequency of point mutations in mitochondrial genome of egg cells of elder women and young women according to embodiments of the present disclosure.
Figure 4:
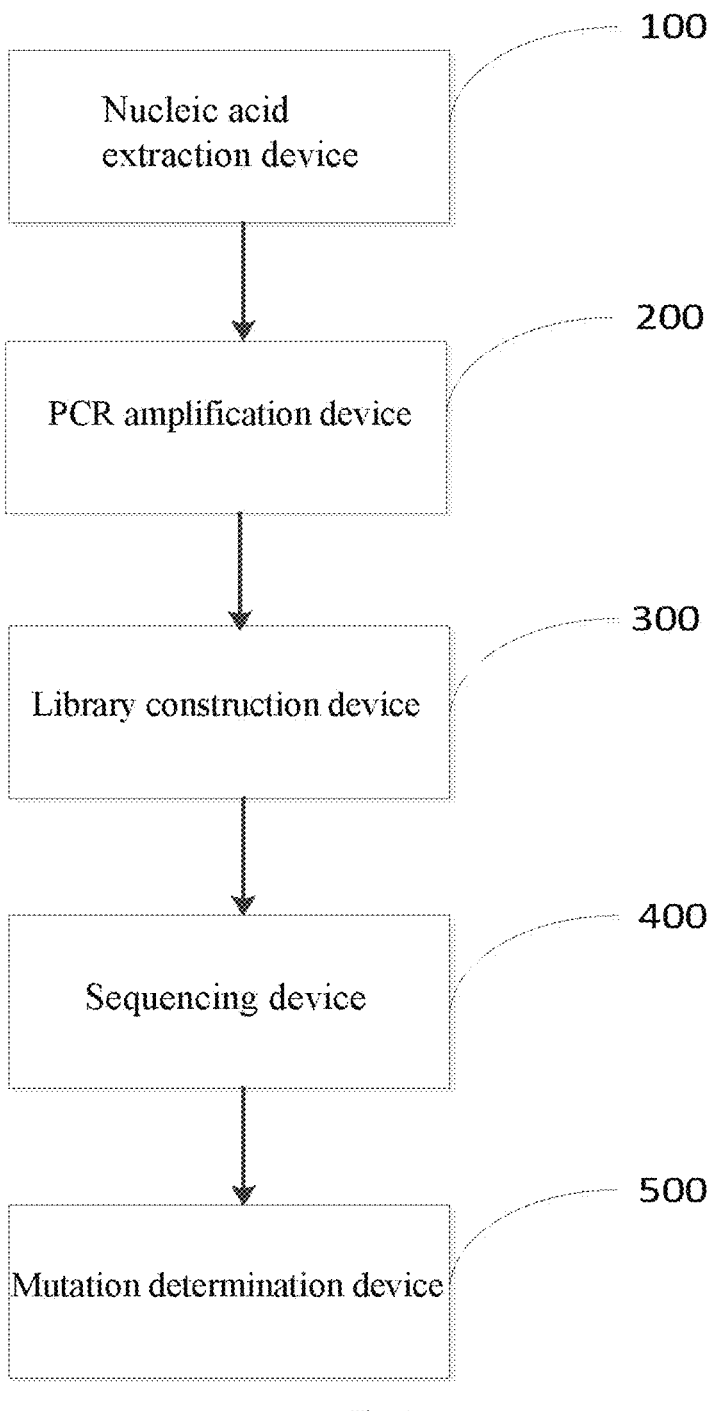
FIG. 4 is a schematic diagram showing the structure of a system for detecting mtDNA mutations according to embodiments of the present disclosure.

FIG. 3 shows the frequency of point mutations in mitochondrial genome of egg cells of 9 young female patients and 10 elderly female patients of the present disclosure. The results showed that the frequency of point mutations in the mitochondrial genome of the egg cells of the elderly female patients was mainly between (0.002, 0.005), and the number of point mutations in the mitochondrial genome of the egg cells of the elderly female patients located within the frequency range was significantly higher than that of the young female patients.

CONCLUSION

The existing technology cannot detect the mitochondrial mutation rate of an egg cell. In contrast, the detection method of the present disclosure is capable of detecting the mtDNA mutations in a trace amount of egg cells, such as one to four egg cells, with remarkably high sensitivity and specificity.

In the description of this specification, reference to terms "an embodiment", "some embodiments", "one embodiment", "an example", "an illustrative example", "some examples" or the like means that a particular feature, structure, material or characteristic described in connection with the embodiment or example is included in at least one embodiment or example of the present disclosure. Thus, the illustrative representations of the terms are not necessarily directed to the same embodiment or example in this specification. Moreover, the specific features, structures, materials or characteristics as described can be combined in any one or more embodiments or examples in a suitable manner. In addition, those skilled persons in the art can combine different embodiments or examples or the features of the different embodiments or examples described in this specification without contradicting each other.

Although the embodiments of the present disclosure have been shown and described above, it can be understood that the embodiments described above are exemplary and should not be construed as limiting the present disclosure. An ordinary skilled person in the art could make changes, modifications, substitutions, and modifications to the embodiments within the scope of the present disclosure.

What is claimed is:

1. A method for detecting mitochondrial DNA (mtDNA) mutations in cells to be tested, comprising:

(a) extracting mtDNA from the cells;

(b) subjecting different predetermined regions of the mtDNA to PCR amplification to obtain amplification products of the different predetermined regions, wherein the different predetermined regions of the mtDNA are superimposed to form a full-length mtDNA;

(c) mixing the amplification products of the different predetermined regions to obtain a nucleic acid sequencing library of the full-length mtDNA;

(d) subjecting the nucleic acid sequencing library to sequencing to obtain a sequencing result; and (e) determining the mtDNA mutations in the cells based on the sequencing result, wherein the number of the cells is one to four, the cell is an egg cell, wherein the different predetermined regions of the mtDNA comprises a mitochondrial genome 3561-9794 region, a mitochondrial genome 9795-14567 region, a mitochondrial genome 14562-139 region and a mitochondrial genome 115-3560 region, wherein primers for the PCR amplification comprise the sequences shown in SEQ ID NOS: 1-8.

2. The method according to claim 1, wherein step (a), extracting mtDNA from the cells is performed by subjecting the cells to a lysis treatment.

3. The method according to claim 1, wherein subjecting different predetermined regions of the mtDNA to PCR amplification is performed by a reaction procedure of:

| | | |
|---|---|---|
| 95° C. | 5 minutes | |
| 94° C. | 30 seconds | 40 cycles |

-continued

| | | |
|---|---|---|
| 57° C. | 45 seconds | |
| 68° C. | 6 minutes and 30 seconds | |
| 68° C. | 10 minutes | |
| 4° C. | holding | | or by a reaction procedure of:

| | | |
|---|---|---|
| 95° C. | 5 minutes | |
| 94° C. | 30 seconds | 40 cycles |
| 57° C. | 45 seconds | |
| 68° C. | 5 minutes | |
| 68° C. | 10 minutes | |
| 4° C. | holding | | or by a reaction procedure of:

| | | |
|---|---|---|
| 95° C. | 5 minutes | |
| 94° C. | 30 seconds | 40 cycles |
| 57° C. | 45 seconds | |
| 68° C. | 2 minutes | |
| 68° C. | 10 minutes | |
| 4° C. | holding | | or by a reaction procedure of:

| | | |
|---|---|---|
| 95° C. | 5 minutes | |
| 94° C. | 30 seconds | 40 cycles |
| 57° C. | 45 seconds | |
| 68° C. | 3 minutes and 30 seconds | |
| 68° C. | 10 minutes | |
| 4° C. | holding. | |

4. The method according to claim 2, wherein the lysis treatment is performed in a lysis solution.

5. The method according to claim 4, wherein the lysis solution in a volume of 20 μL comprises 17 to 18 μL of $H_2O$, 1 to 3 μL of 10×KOD buffer and 0.2 to 0.3 μL of proteinase K.

6. The method according to claim 4, wherein a ratio of the cells to the lysis solution is 1 to 4 cells per 20 μL lysis solution.

7. The method according to claim 4, wherein the lysis treatment comprises lysing at 50-60° C. for 40-50 minutes, subsequently at 90-100° C. for 1-10 minutes and holding at 1-10° C.

\* \* \* \* \*

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: 3561-FP

<400> SEQUENCE: 1 atgaacccc ctccccatac cc                                          22

<210> SEQ ID NO 2
<211> LENGTH: 27
<212> TYPE: DNA
<213> ORGANISM: Artificial Sequence
<220> FEATURE:
<223> OTHER INFORMATION: h1-9794-R1

<400> SEQUENCE: 2
tgttgagccg tagatgccgt cggaaat                                    27

<210> SEQ ID NO 3
<211> LENGTH: 29
<212> TYPE: DNA
<213> ORGANISM: Artificial Sequence
<220> FEATURE:
<223> OTHER INFORMATION: h1-9795-F2

<400> SEQUENCE: 3 tttttttgtag ccacaggctt ccacggact                                 29

<210> SEQ ID NO 4
<211> LENGTH: 24
<212> TYPE: DNA
<213> ORGANISM: Artificial Sequence
<220> FEATURE:
<223> OTHER INFORMATION: h1-14567-R2

<400> SEQUENCE: 4
tgtggtcggg tgtgttatta ttct                                       24

<210> SEQ ID NO 5
<211> LENGTH: 20
<212> TYPE: DNA
<213> ORGANISM: Artificial Sequence
<220> FEATURE:
```

-continued

<223> OTHER INFORMATION: h1-14562-F3

<400> SEQUENCE: 5
ccacaccgct aacaatcaat                                          20

<210> SEQ ID NO 6
<211> LENGTH: 25
<212> TYPE: DNA
<213> ORGANISM: Artificial Sequence
<220> FEATURE:
<223> OTHER INFORMATION: h1-139-R3

<400> SEQUENCE: 6
gaatcaaaga cagatactgc gacat                                    25

<210> SEQ ID NO 7
<211> LENGTH: 25
<212> TYPE: DNA
<213> ORGANISM: Artificial Sequence
<220> FEATURE:
<223> OTHER INFORMATION: h1-115-F4

<400> SEQUENCE: 7
atgtcgcagt atctgtcttt gattc                                    25

<210> SEQ ID NO 8
<211> LENGTH: 20
<212> TYPE: DNA
<213> ORGANISM: Artificial Sequence
<220> FEATURE:
<223> OTHER INFORMATION: 3560-RP

<400> SEQUENCE: 8
agtagaagag cgatggtgag                                          20

<210> SEQ ID NO 9
<211> LENGTH: 20
<212> TYPE: DNA
<213> ORGANISM: Artificial Sequence
<220> FEATURE:
<223> OTHER INFORMATION: 11509-RP

<400> SEQUENCE: 9
gagaatgagt gtgaggcgta                                          20

<210> SEQ ID NO 10
<211> LENGTH: 21
<212> TYPE: DNA
<213> ORGANISM: Artificial Sequence
<220> FEATURE:
<223> OTHER INFORMATION: 11493-FP

<400> SEQUENCE: 10
gcctcacact cattctcaac c                                        21

<210> SEQ ID NO 11
<211> LENGTH: 20
<212> TYPE: DNA
<213> ORGANISM: Artificial Sequence
<220> FEATURE:
<223> OTHER INFORMATION: 7781-RP

<400> SEQUENCE: 11
ttcagacggt ttctatttcc                                          20

-continued

```
<210> SEQ ID NO 12
<211> LENGTH: 22
<212> TYPE: DNA
<213> ORGANISM: Artificial Sequence
<220> FEATURE:
<223> OTHER INFORMATION: 7767-FP

<400> SEQUENCE: 12
tagaaaccgt ctgaactatc ct                                          22

<210> SEQ ID NO 13
<211> LENGTH: 20
<212> TYPE: DNA
<213> ORGANISM: Artificial Sequence
<220> FEATURE:
<223> OTHER INFORMATION: 15557-RP

<400> SEQUENCE: 13
cgggcttgat gtggggaggg                                             20

<210> SEQ ID NO 14
<211> LENGTH: 20
<212> TYPE: DNA
<213> ORGANISM: Artificial Sequence
<220> FEATURE:
<223> OTHER INFORMATION: 15534-FP

<400> SEQUENCE: 14
acacccctcc ccacatcaag                                             20
```